US010053938B2

(12) United States Patent
Gupta et al.

(10) Patent No.: US 10,053,938 B2
(45) Date of Patent: Aug. 21, 2018

(54) METHODS AND APPARATUS FOR COLLECTING AND PRESERVING CORE SAMPLES FROM A RESERVOIR

(71) Applicant: Aramco Services Company, Houston, TX (US)

(72) Inventors: Anuj Gupta, Katy, TX (US); Daniel T. Georgi, Houston, TX (US); Katherine L. Hull, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/791,993

(22) Filed: Oct. 24, 2017

(65) Prior Publication Data

US 2018/0058163 A1     Mar. 1, 2018

Related U.S. Application Data

(62) Division of application No. 15/280,368, filed on Sep. 29, 2016, now Pat. No. 9,828,820.
(Continued)

(51) Int. Cl.
*G01V 5/00*         (2006.01)
*E21B 25/08*      (2006.01)
(Continued)

(52) U.S. Cl.
CPC ............ *E21B 25/08* (2013.01); *E21B 25/005* (2013.01); *E21B 49/06* (2013.01); *E21B 49/082* (2013.01);
(Continued)

(58) Field of Classification Search
CPC ........ E21B 49/06; E21B 49/10; E21B 49/006; E21B 25/10; E21B 25/02
See application file for complete search history.

(56) References Cited

U.S. PATENT DOCUMENTS 2,880,969 A    4/1959   Williams
2,915,284 A    12/1959   Ortloff
(Continued)

FOREIGN PATENT DOCUMENTS

GB          1044218 A      9/1966
RU        2012132365 A    2/2014

OTHER PUBLICATIONS

Agarwal et al., "Rotary sidewall coring—size matters," Winter 2013/2014, Oilfield Review, pp. 30-39.*
(Continued)

*Primary Examiner* — Kiho Kim
(74) *Attorney, Agent, or Firm* — Bracewell LLP; Constance G. Rhebergen; Brian H. Tompkins

(57) ABSTRACT

Provided herein are methods and apparatus for collecting and preserving core samples from a reservoir. In some embodiments, a method includes obtaining core samples from a reservoir using a rock and fluid sampling tool and depositing the core samples in a vessel filled with a hydrogen-free fluid such that a portion of the hydrogen-free fluid is displaced by the core samples and the core samples are immersed in the hydrogen-free fluid. The method also includes transferring a gas into the vessel to occupy a space in the vessel and sealing the vessel via a cap on an end of the vessel. Methods of analyzing the core samples core samples collected from a reservoir and a rock and fluid sampling tool are also provided.

10 Claims, 6 Drawing Sheets

Related U.S. Application Data

(60) Provisional application No. 62/235,132, filed on Sep. 30, 2015.

(51) Int. Cl.
| | |
|---|---|
| *E21B 49/08* | (2006.01) |
| *G01V 5/04* | (2006.01) |
| *G01N 33/24* | (2006.01) |
| *E21B 49/06* | (2006.01) |
| *E21B 25/00* | (2006.01) |
| *G01N 23/046* | (2018.01) |

(52) U.S. Cl.
CPC ........... *E21B 49/086* (2013.01); *G01N 33/24* (2013.01); *G01V 5/04* (2013.01); *G01N 23/046* (2013.01)

(56) References Cited

U.S. PATENT DOCUMENTS

| | | | |
|---|---|---|---|
| 3,454,117 A | 7/1969 | Eckel | |
| 3,548,958 A | 12/1970 | Blackwell et al. | |
| 4,142,594 A | 3/1979 | Thompson | |
| 4,317,490 A | 8/1984 | Jageler | |
| 4,466,495 A | 8/1984 | Jageler | |
| 4,540,882 A | 9/1985 | Vinegar | |
| 4,557,152 A | 12/1985 | Plessers et al. | |
| 4,716,974 A | 1/1988 | Radford | |
| 4,950,844 A | 8/1990 | Hallmark et al. | |
| 5,360,074 A | 11/1994 | Collee | |
| 5,482,122 A * | 1/1996 | Abass | E21B 43/26 166/250.01 |
| 5,482,123 A | 1/1996 | Collee | |
| 5,546,798 A | 8/1996 | Collee | |
| 5,560,438 A | 10/1996 | Collee | |
| 5,804,820 A | 9/1998 | Evans et al. | |
| 6,230,825 B1 | 5/2001 | Aumann | |
| 6,283,228 B2 | 9/2001 | Collee | |
| 6,659,204 B2 | 12/2003 | Aumann | |
| 8,307,704 B2 | 11/2012 | Georgi et al. | |
| 8,739,899 B2 | 6/2014 | Kumar | |
| 9,482,089 B2 * | 11/2016 | Delmar | E21B 43/34 |
| 2006/0081398 A1 * | 4/2006 | Arian | E21B 49/06 175/58 |
| 2006/0102343 A1 * | 5/2006 | Skinner | E21B 7/15 166/250.1 |
| 2009/0164128 A1 * | 6/2009 | Tchakarov | E21B 49/006 702/11 |
| 2010/0282515 A1 * | 11/2010 | Reid, Jr. | E21B 49/06 175/58 |
| 2012/0204781 A1 | 8/2012 | Chun et al. | |
| 2014/0262527 A1 | 9/2014 | Rothenwaender et al. | |
| 2015/0191985 A1 | 7/2015 | Berger | |

OTHER PUBLICATIONS

Electronics Markets Materials Division "Flurolnert liquids for electronic manufacturing" Dec. 10, 2003 pp. 1-4.

Ersland, G. et al. "Complementary imaging of oil recovery mechanisms in fractured reservoirs" Chemical Engineering Journal 158 (2010) 32-38.

Geotek Pressure Core Analysis available as of Sep. 28, 2016 at the website:http://www.geoteck.co.uk/services/pressure_core_analysis; pp. 1-3.

Halliburton "CoreVault Fluid and Rock Sampling System" available as of Sep. 29, 2016 at the website: http://www.halliburton.com/public/lp/contents/Data_Sheets/web/H/H011158.pdf; pp. 1-2.

Halliburton "CoreVault System" available as of Sep. 28, 2016 at the website: http://www.halliburton.com/en-US/ps/wireline-perforating/wireline-and-perforating/open-hole-logging/sidewall-coring/corevault.page?node-id=hfqelaci; p. 1.

Halliburton "New CoreVault service helped operator confirm 2.5 times more gas in place than expected" available as of Sep. 29, 2016 at the website: http://www.halliburton.com/public/lp/contents/Case_Histories/web/H010950.pdf; pp. 1-4.

Halliburton "Operators Maximize Economic Value of Their Assets with CoreVault System" available as of Sep. 29, 2016 at the website: http://www.halliburton.com/public/lp/contents/Case_Histories/web/CoreVault-Bakken.pdf; pp. 1-2.

International Search Report and Written Opinion for related PCT application PCT/US2016/054593 (ASC0010/PCT) dated Mar. 16, 2017, 18 pgs.

McFall, Alan L. "The Construction and Evaluation of an Improved Pressure Coring System," Sandia Laboratories; published Aug. 22, 1979; pp. 1-6.

Partial International Search for International Application No. PCT/US2016/054593 (ASC0010/PCT); International Filing Date Sep. 30, 2016; dated Jan. 11, 2017 (7 pages).

Pinkett, John et al.; "Innovative Sidewall Pressure Coring Technology Improves Reservoir Insight in Multiple Applications" SPWLA 57th Annual Logging Symposium, Jun. 25-29, 2016; pp. 1-15.

* cited by examiner

METHODS AND APPARATUS FOR COLLECTING AND PRESERVING CORE SAMPLES FROM A RESERVOIR

CROSS-REFERENCE TO RELATED PATENT APPLICATIONS

This application is a divisional of and claims priority to U.S. application Ser. No. 15/280,368, filed Sep. 29, 2016, and titled "METHODS AND APPARATUS for COLLECTING and PRESERVING CORE SAMPLES FROM A RESERVOIR," which claims priority to U.S. Provisional Application No. 62/235,132, filed Sep. 30, 2015, and titled "METHODS AND APPARATUS for COLLECTING and PRESERVING CORE SAMPLES FROM A RESERVOIR." For purposes of United States patent practice, this application incorporates the contents of the Provisional application by reference in its entirety.

BACKGROUND

Field of the Invention

Embodiments of the disclosure generally relate to obtaining and analyzing core samples from geological formations. More specifically, the present disclosure relates to methods and systems for preserving original pore fluids and rock properties in collected core samples and enabling effective imaging of such samples.

Description of the Related Art

Wells may be drilled into rocks to access fluids stored in geological formations having hydrocarbons. Such a geological formation may be referred to as a "reservoir." A variety of techniques exist for determining the presence and amount of hydrocarbons in such reservoirs. In some instances, a sample of rock and fluids (referred to as a "core sample") may be collected downhole in the wellbore of the well and retrieved to the surface for further analysis. The core sample may be analyzed to quantify the amount and value of hydrocarbons (e.g., oil and gas) in the reservoir. The analysis of a core sample may also determine the rate at which the identified oil and gas may be produced and aid in identifying techniques for extracting the oil and gas and maximizing recovery from the reservoir.

However, obtaining an unaltered core sample from a reservoir may be challenging and may impact accurate analysis of the sample and subsequent quantification of hydrocarbons in the reservoir. Existing techniques for obtaining a core sample from a reservoir may stress the rocks and fluids in the sample and cause changes in the rock properties, fluid properties, or both. Additionally, core samples obtained by existing techniques may have fluid compositions that differ from the native fluid compositions, especially for core samples of rock having a relatively low permeability. Moreover, for hydrocarbons such as tight shale gas and tight shale oil, it may be difficult to obtain the original gas-in-place, and a core sample from such reservoirs may contain volatile fluids and highly compressible gases that expand as the sample is depressurized during retrieval to the surface, further impacting analysis of the core sample.

SUMMARY

Embodiments of the disclosure generally relate to methods and systems for collecting one or more core samples and analyzing one or more core samples. In some embodiments, a method is provided that includes obtaining one or more core samples from a reservoir using a rock and fluid sampling tool inserted downhole in a wellbore extending from a surface into the reservoir. The rock and fluid sampling tool includes a vessel filled with a hydrogen-free fluid. The method further includes depositing the one or more core samples in the vessel such that a portion of the hydrogen-free fluid is displaced by the one or more core samples and the one or more core samples are immersed in the hydrogen-free fluid. The vessel further includes a space unoccupied by the one or more core samples and the hydrogen-free fluid. The method also includes transferring a gas into the vessel to fill the unoccupied space and sealing the vessel via a cap on an end of the vessel.

In some embodiments, sealing the vessel via the cap produces a pressurized vessel at a pressure value. In some embodiments, the pressure value is substantially equal to a pressure of the reservoir. In some embodiments, the method includes retrieving the rock and fluid sampling tool having the sealed vessel from downhole in the wellbore to the surface. In some embodiments, the method includes imaging at least one of the one or more core samples in the pressurized vessel using at least one of neutron imaging, X-ray imaging, and nuclear magnetic resonance imaging. In some embodiments, obtaining the one or more core samples from the reservoir using the rock and fluid sampling tool includes obtaining the one or more core samples from a sidewall of the wellbore using a rotary coring device.

In some embodiments, the hydrogen-free fluid is a fluorocarbon-based fluid. In some embodiments, the gas includes nitrogen. In some embodiments, the vessel includes a eutectic metal component. In some embodiments, the method includes inserting the rock and fluid sampling tool in the wellbore. In some embodiments, the method includes adding the hydrogen-free fluid to the vessel before inserting the rock and fluid sampling tool in the wellbore. In some embodiments, obtaining one or more core samples from the reservoir using the rock and fluid sampling tool inserted downhole in the wellbore includes obtaining a first core sample at a first depth in the wellbore and obtaining a second core sample at second depth in the wellbore.

In some embodiments, the method includes removing an amount of the gas, an amount of the hydrogen-free fluid, or both. In some embodiments, the method further includes transferring an aqueous solution to the vessel to replace the removed amount of the gas, the removed amount of the hydrogen-free fluid, or both. In some embodiments, the method further includes imaging at least one core sample of the one or more core samples in the vessel using at least one of neutron imaging and computed tomography (CT) imaging. In some embodiments, the method also includes determining saturation of the aqueous solution into the at least one core sample.

In some embodiments, the method includes removing an amount of the gas, an amount of the hydrogen-free fluid, or both. In some embodiments, the method also includes transferring carbon dioxide to the vessel to replace the removed amount of the gas, the removed amount of the hydrogen-free fluid, or both. In some embodiments, the method includes imaging at least one core sample of the one or more core samples in the vessel using computed tomography (CT) imaging. The method also includes determining imbibition of the carbon dioxide into the at least one core sample. In some embodiments, the method also includes determining an exchange of the carbon dioxide with a fluid of the at least one core sample.

In some embodiments, the method includes removing an amount of the gas, an amount of the hydrogen-free fluid, or both and transferring diborane to the vessel to replace the removed amount of the gas, the removed amount of the hydrogen-free fluid, or both. The method further includes imaging at least one core sample of the one or more core samples in the vessel using neutron imaging.

In another embodiment, a method of analyzing core samples collected from a reservoir is provided. The method includes providing a pressurized vessel having one or more core samples immersed in a hydrogen-free fluid. The pressurized vessel has a gas and is sealed downhole in a wellbore extending into a reservoir after collecting the one or more core samples from the reservoir. The method also includes heating the pressurized vessel to a temperature value and reducing, in one or more steps, a pressure of the pressurized vessel to atmospheric pressure. The one or more steps include releasing an amount of the gas, an amount of the hydrogen-free fluid, or both to reduce the pressure of the pressurized vessel by a pressure value and determining the released amount of the gas, the released amount of the hydrogen-free fluid, or both. The method also includes determining, after reducing the pressure of the pressurized vessel to atmospheric pressure, a total amount of the gas, the hydrogen-free fluid, and hydrocarbons released and calculating a hydrocarbons-in-place value from the total amount of gas, hydrogen-free fluid, and hydrocarbons released.

In some embodiments, the temperature value is substantially equal to a temperature of the reservoir. In some embodiments, the pressure value is a first pressure value and the method includes pressuring the pressurized vessel to a second pressure value before reducing, in one or more steps, the pressure of the pressurized vessel to atmospheric pressure. In some embodiments, the second pressure value is substantially equal to a pressure of the reservoir.

In some embodiments, a rock and fluid sampling tool is provided. The rock and fluid sampling tool includes a rotary sidewall coring device and a vessel having a eutectic metal component, the vessel configured to contain one or more core samples of a reservoir. The one or more core samples are obtained by the rotary sidewall coring device from a sidewall of a wellbore extending from a surface into a reservoir. The rock and fluid sampling tool further includes a container configured to store a gas and one or more valves connecting the container to the vessel. In some embodiments, the rock and fluid sampling tool is a wireline rock and fluid sampling tool.

In some embodiments, a method of collecting one or more core samples from a wellbore. The method includes inserting a rock and fluid sampling tool in a wellbore extending from a surface into a reservoir and extracting a core sample from a sidewall of the wellbore. The method also includes placing the core sample in a vessel, the vessel containing a hydrogen-free fluid sealing the vessel, transferring a gas into the vessel, and retrieving the vessel to the surface. In some embodiments, the inserting a rock and fluid sampling tool in a wellbore comprises includes the rock and fluid sampling tool on a wireline inserted in the wellbore.

BRIEF DESCRIPTION OF THE DRAWINGS

These and other features, aspects, and advantages of the present disclosure will become better understood with regard to the following descriptions, claims, and accompanying drawings. It is to be noted, however, that the drawings illustrate only several embodiments of the disclosure and are therefore not to be considered limiting of the scope of the disclosure as it can admit to other equally effective embodiments.

DETAILED DESCRIPTION

Figure 1:
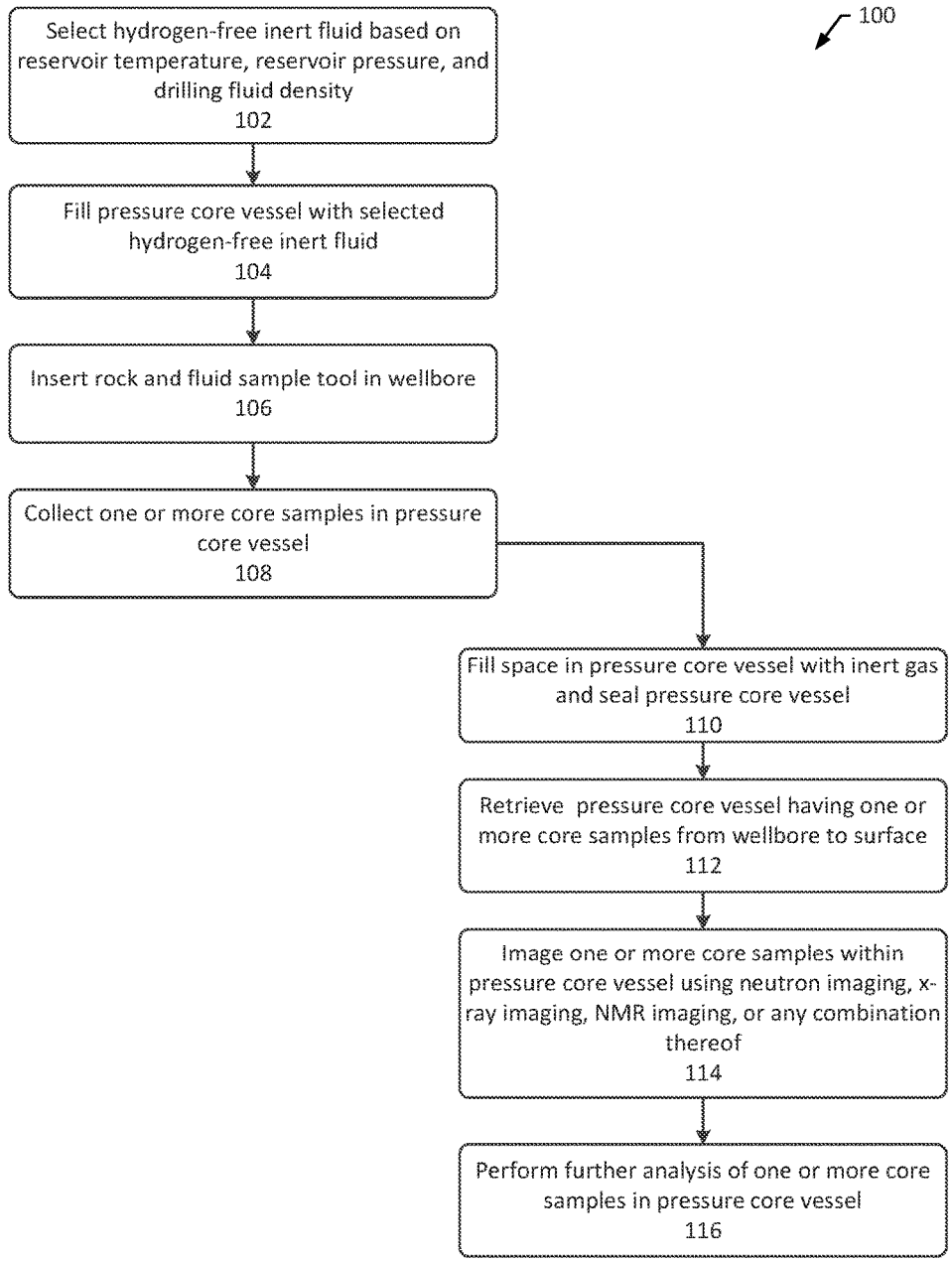
FIG. 1 is a block diagram of a process for collecting one or more core samples and preserving original pore fluids and rock properties in accordance with an embodiment of the disclosure.

The present disclosure will now be described more fully hereinafter with reference to the accompanying drawings, which illustrate embodiments of the disclosure. The disclosure may, however, be embodied in many different forms and should not be construed as limited to the illustrated embodiments set forth herein. Rather, these embodiments are provided so that this disclosure will be thorough and complete, and will fully convey the scope of the disclosure to those skilled in the art.

Rock and fluid sampling systems may provide for the downhole collection of core samples (e.g., rock and fluid samples) from a well in a reservoir. In some instances, the core samples may be collected and sealed in a vessel (referred to as "pressure coring"). Some rock and fluid sampling systems may prefill the vessel with a sodium formate solution and seal the vessel after samples are collected and placed in the vessel. However, as the vessel cools during its ascent from downhole to the surface, the vessel may lose pressure due to shrinking of fluids inside the vessel. Consequently, fluids inside the core samples may be expelled. Additionally, the aqueous phase of the sodium formate may imbibe into the water-wet portions of the core samples, expelling hydrocarbons and affecting the subsequent analysis of water imbibition into the core samples. The aqueous phase of the sodium formate may also interact with water-sensitive portions of the rock of the core samples and may alter properties of such water-sensitive portions.

With the foregoing in mind, embodiments of the disclosure include methods, apparatus, and systems for collecting and preserving core samples from a reservoir and analyzing the preserved core samples in a pressure core vessel (PCV). The techniques described herein may provide for maintenance of the original reservoir pressure in the pressure core vessel, thus preventing the expelling of fluids inside the core samples or gases separating from liquid phases of fluids inside the core samples. Thus, the techniques described herein may enable fluids to be imaged in their original pore location inside rocks of the core samples. Additionally, the techniques described herein may prevent imbibition or other entry of foreign fluids into the core samples and enable subsequent analysis of water and water-based fluid imbibition into the core samples after the pressure core vessel is retrieved to the surface. Additionally, the techniques described herein may provide for neutron imaging, X-ray imaging, and nuclear magnetic resonance (NMR) imaging of the core samples at reservoir pressure while the core samples remain in the pressure core vessel.

As explained below, a pressure core vessel for collecting core samples may be filled with a hydrogen-free fluid (which may include or be referred to as a "hydrogen-free inert fluid") before collection of core samples from a reservoir accessible in a wellbore of a well. As used herein, the term "filled" does not require the entire volume of the pressure core vessel be occupied. In some embodiments, the specific gravity of the hydrogen-free fluid may be selected based on reservoir pressure reservoir temperature, and density of a drilling fluid used during a drilling operation of the well, so that the specific gravity of the hydrogen-free fluid is greater than the specific gravity of a drilling fluid used during a drilling operation of the well. As a core sample is deposited into the pressure core vessel, the hydrogen-free fluid may be displaced and occupy the space above the core sample, thus immersing the core sample and preventing further contamination of the core sample by the drilling fluid.

In some embodiments, a gas (e.g., an inert gas such as nitrogen or another inert gas) may be transferred into the pressure core vessel to occupy some space in the pressure core vessel (e.g., space unoccupied by the hydrogen-free fluid and the collected core samples, such as the space above the hydrogen-free fluid). In some embodiments, a rock and fluid sampling tool for collecting and preserving core samples may include valves and other components to facilitate the transfer of a gas (e.g., an insert gas such as nitrogen or another inert gas) into the pressure core vessel. As will be appreciated, the space in the pressure core vessel occupied by the gas may minimize depressurization of core samples as the pressure core vessel is retrieved to the surface.

After the pressure core vessel is retrieved to the surface, the collected core samples may be analyzed inside the pressure core vessel using various imaging techniques such as neutron imaging, X-ray imaging, and NMR imaging, as the hydrogen-free fluid in the pressure core vessel does not emit a spectroscopically detectable signature when subjected to these imaging techniques (i.e., the hydrogen-free fluid is transparent to neutrons and does not have an H-NMR signal). In some embodiments, the pressure core vessel may be pressurized to the original reservoir pressure (if the pressure core vessel is not at the original reservoir pressure) and heated to the original reservoir temperature to enable quantification of the amount of hydrocarbons in the reservoir sample. After the core samples in the pressure core vessel have equilibrated, the pressure inside the pressurized core vessel may be reduced in steps and the amount of gas and fluids (including, for example, gas previously added to the vessel, the hydrogen-free fluid, and hydrocarbons) released and collected at each pressure reduction may be recorded. The pressure reduction and recordation of released gas and fluids may be repeated until the pressure core vessel is depressurized to atmospheric pressure. The total volume of gas and fluids released during the depressurization may provide an estimate of the hydrocarbons-in-place of the reservoir.

In some embodiments, the added gas and the hydrogen-free fluid in the vessel may be replaced by an aqueous solution to determine imbibition of water or water-based fluid into collected core samples. In some embodiments, the gas and the hydrogen-free fluid in the pressure core vessel may be replaced by an aqueous solution via injection of the aqueous solution at the top of the pressure core vessel and withdrawal of the hydrogen-free fluid from the bottom of the pressure core vessel. The saturation of the aqueous solution (e.g., imbibition of an aqueous phase of the solution) into the core samples may be monitored via neutron imaging, computed tomography (CT) imaging, or both.

In some embodiments, the gas in the pressure core vessel may be removed and replaced by relatively high pressure carbon dioxide. In such embodiments, the hydrogen-free fluid in the vessel may be withdrawn from the bottom of the vessel as carbon dioxide is transferred into the vessel. In such embodiments, the pressure in the pressure core vessel may be maintained during the transfer of carbon dioxide into the pressure core vessel. The imbibition of the carbon dioxide or exchange of the carbon dioxide with gases or fluids in the core samples may be monitoring using, for example, CT imaging. In some embodiments, the gas in the pressure core vessel may be removed and replaced by diborane ($B_2H_6$). In such embodiments, the diborane ($B_2H_6$) may enable the use of high contrast neutron imaging to obtain images of core samples in the pressure core vessel. In other embodiments, other gases having a large neutron signal and that may enhance contrast in neutron imaging may be used such as, for example, trimethylborane (($CH_3$)$_3$B), tetraborane ($B_4H_{11}$), boron trifluoride ($BF_3$), or boron trichloride ($BCl_3$) In other embodiments, liquids having a large neutron signal and that may enhance contrast in neutron imaging may also be used such as, for example, pentaborane ($B_5H_9$), hexaborane ($B_6H_{10}$), triethylborane (B($C_2H_5$)$_3$), trimethylborate (B($OCH_3$)$_3$), triethylborate (B($OC_2H_5$)$_3$), tris(trimethylsiloxy)borate ((($CH_3$)$_3$SiO)$_3$B), boron tribromide ($BBr_3$), borazine ($BH_3NH_3$), phenylboron dichloride ($C_6H_5BCl_2$), tetrafluoroboric acid ($HBF_4$), tri-n-butylborate (B($OC_4H_9$)$_3$), trimethoxyboroxine (($CH_3O$)$_3B_3O_3$), tri-i-propylborate (B($OCH(CH_3)_2$)$_3$). In other embodiments, liquid adducts of borane or borone derivatives may also be used including, for example, borane-pyridine ($C_5H_5N$:$BH_3$), borane-dimethyl sulfide (($CH_3$)$_2$S:$BH_3$), boron trifluoride-acetic acid ($BF_3$:$2CH_3COOH$), boron trifluoride-ethyl ether ($BF_3$:$O(C_2H_5)_2$), Embodiments of the disclosure may include or be implemented in a rock and fluid sampling tool having the pressure core vessel. In some embodiments, for example, a rock and fluid sampling system may include a rotary sidewall coring device that collects one or more sidewall core samples in the pressure core vessel such that the core samples are preserved in the manner described herein. In some embodiments, the rock and fluid sampling tool may be a wireline tool to provide insertion into the wellbore. In some embodiments, the rock and fluid sampling tool may include a pressure core vessel formed with a eutectic metal component, such as a eutectic metal insert contained in the pressure vessel. In some embodiments, a rock and fluid sampling system may include the aforementioned rock and fluid sampling tool and may include a conveyance system (e.g., a wireline system) and a control system.

FIG. 1 depicts a process 100 for collecting and preserving one or more core samples from a reservoir in accordance with an embodiment of the disclosure. As described below, the process 100 may enable the original pore fluids and rock properties of the one or more core samples to be preserved during collection and retrieval of the one or more core samples. Initially, a hydrogen-free fluid for use in a rock and fluid sampling tool may be selected based on reservoir temperature, reservoir pressure, drilling fluid density, or any combination of these factors (block 102). For example, in some embodiments, reservoir conditions such as reservoir temperature and reservoir pressure may be obtained from the wellbore during drilling (e.g., via a measurement-while-drilling (MWD) tool) or other operations. In some embodiments, the hydrogen-free fluid may be a fluorocarbon-based fluid, such as one of the Fluorinert™ group of fluids manufactured by 3M of Maplewood, Minn., USA. In such embodiments, the specific gravity of a selected fluorocarbon-based fluid may be based on the reservoir temperature, reservoir pressure, drilling fluid density, or combination of these factors. The selected hydrogen-free fluid in the pressure core vessel may not interact with reservoir rock and fluids of the collected core samples and may aid in maintaining pressure in the pressure core vessel. Moreover, as explained further below, the hydrogen-free fluid in the pressure core vessel does not emit a spectroscopically detectable signature to certain imaging techniques, thus enhancing subsequent neutron, x-ray, and NMR imaging of core samples after the pressure core vessel is retrieved to the surface.

Next, the pressure core vessel of the rock and fluid sampling tool may be filled with the selected hydrogen-free fluid (block 104), and the rock and fluid sampling tool may be inserted in the wellbore (block 106). In some embodiments, the rock and fluid sampling tool may be a wireline tool that is run on wireline in the wellbore. In other embodiments, different conveyance systems may be used to insert the rock and fluid sampling tool. Next, one or more core samples may be collected in the pressure core vessel via the rock and fluid sampling tool (block 108). Collection of a core sample may include cutting a sample of reservoir rock and fluid and depositing the sample in the pressure core vessel. In some embodiments, the one or more core samples may include sidewall cores obtained from a side of the wellbore. For example, in some embodiments the reservoir rock and fluid sample may be cut using a rotary sidewall coring device of the rock and fluid sampling tool. As will be appreciated, in such embodiments multiple core samples may be collected at different depths in the wellbore. For example, a first core sample may be collected at a first depth, a second core sample may be collected at a second depth, and so on.

As a core sample is collected in the pressure core vessel, the core sample displaces the hydrogen-free fluid in the pressure core vessel, such that the core sample is immersed in the hydrogen-free fluid and preventing or minimizing contamination and alteration of the core sample (e.g., contamination and alteration by drilling fluid). For example, in a vertical orientation of the rock and fluid sampling tool, the level of the hydrogen-free fluid may increase towards the top of the pressure core vessel as the core samples are immersed and the hydrogen-free fluid is displaced, thus ensuring coverage of all of the core samples collected in the pressure core vessel and preventing further contamination of collected core samples.

After all core samples are collected, the pressure core vessel may include space unoccupied by the core samples and the hydrogen-free fluid. A gas (e.g., an inert gas) may be transferred to the pressure vessel to occupy some of this space and the vessel may be sealed by a sealing cap (block 110). In some embodiments, the gas may include nitrogen. In some embodiments, the gas may be a combination of nitrogen and other inert gases. As will be appreciated, the transferred gas may form a "cushion" above the one or more core samples immersed in the hydrogen-free fluid (e.g., between the top of the pressure core vessel and the one or more core samples and hydrogen-free fluid.) The space occupied by the transferred gas in the pressure core vessel may prevent or minimize depressurization of the one or more core samples as the pressure core vessel is retrieved to the surface.

The pressure core vessel may then be retrieved from the wellbore to the surface (block 112). For example, the rock and fluid sampling tool that includes the pressure core vessel may be retrieved from the wellbore to the surface, such as via a wireline inserted in the wellbore. As the pressure core vessel is retrieved to the surface, the gas in the pressure core vessel may minimize depressurization of the one or more core samples, thus enabling the pressure core vessel to be retrieved to the surface at or near downhole hydrostatic pressure. In some embodiments, the pressure core vessel may have a eutectic metal component (e.g., a eutectic metal insert), such that cooling and the associated depressurization of the one or more core samples may be further prevented or minimized. In such embodiments, the combination of the transferred gas and the eutectic metal component may further prevent or minimize pressure reduction from the original reservoir pressure during retrieval of the pressure core vessel to the surface.

After retrieval of the pressure core vessel to the surface, the one or more core samples in the pressure core vessel may be imaged using one or more imaging techniques, such as neutron imaging, X-ray imaging, NMR imaging, or a combination thereof (block 114). The hydrogen-free fluid does not emit a spectroscopically detectable signature when subjected to these imaging techniques (i.e., the hydrogen-free fluid is transparent to neutrons and does not have an H-NMR signal) and thus does not contribute to the neutron imaging and NMR imaging of the one or more core samples. Thus, the pressure core vessel filled with the hydrogen-free fluid may provide for both neutron imaging and NMR imaging of the one or more core samples that is unaffected by the fluid used to maintain the confining pressure while they remain immersed in the hydrogen-free fluid and without opening the vessel and removing the one or more core samples. Further, the hydrogen-free fluid and the transferred gas in the pressure core vessel do not imbibe into or displace fluids inside the one or more core samples, thus enabling pore fluids to be imaged in their original locations in the one or more core samples. In some embodiments, further analysis of the one or more core samples in the pressure vessel may be performed (block 116), as described below.

Figure 2:
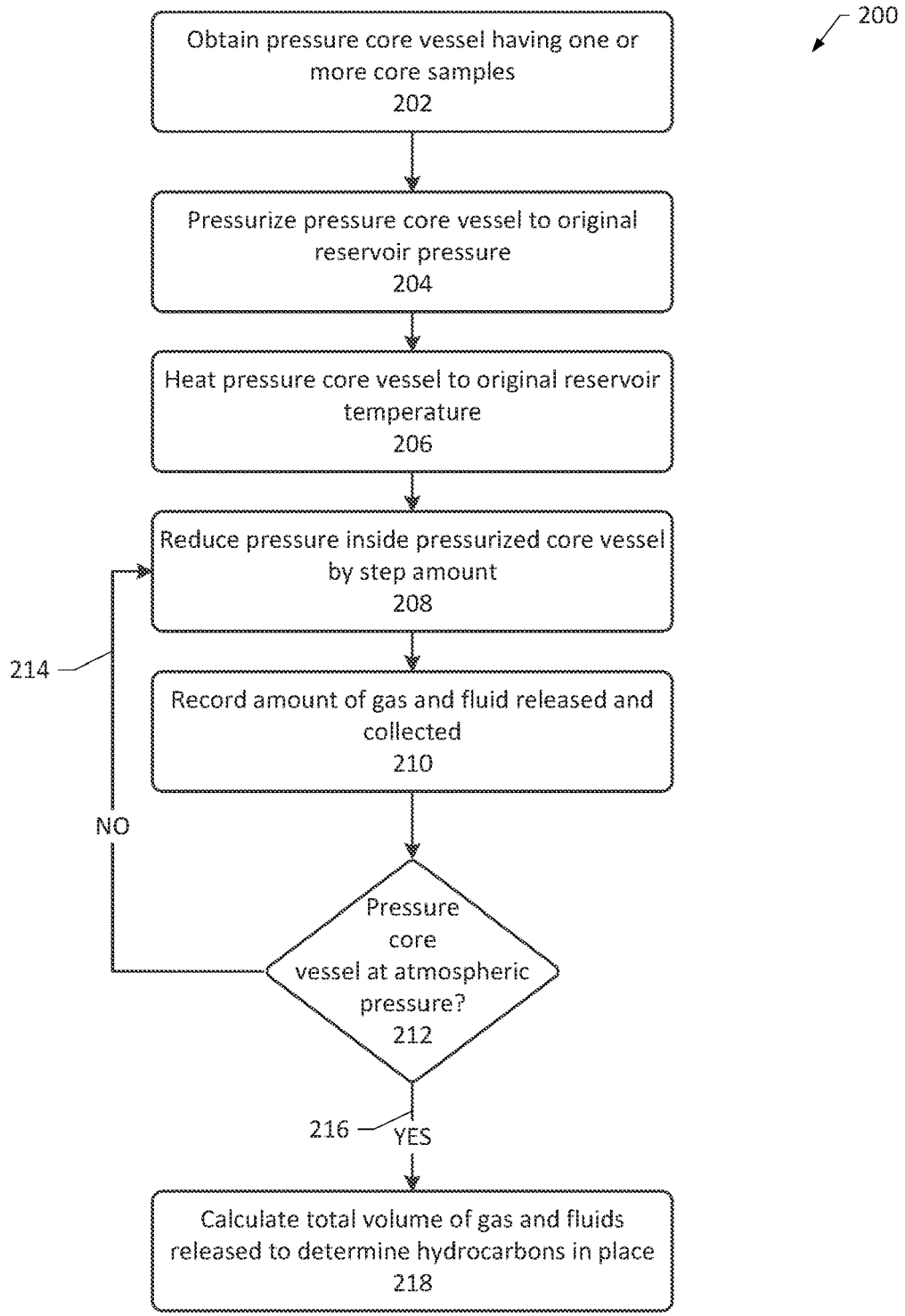
FIG. 2 is a block diagram of a process for determining hydrocarbons-in-place from one or more core samples collected in accordance with an embodiment of the disclosure.
Figure 3:
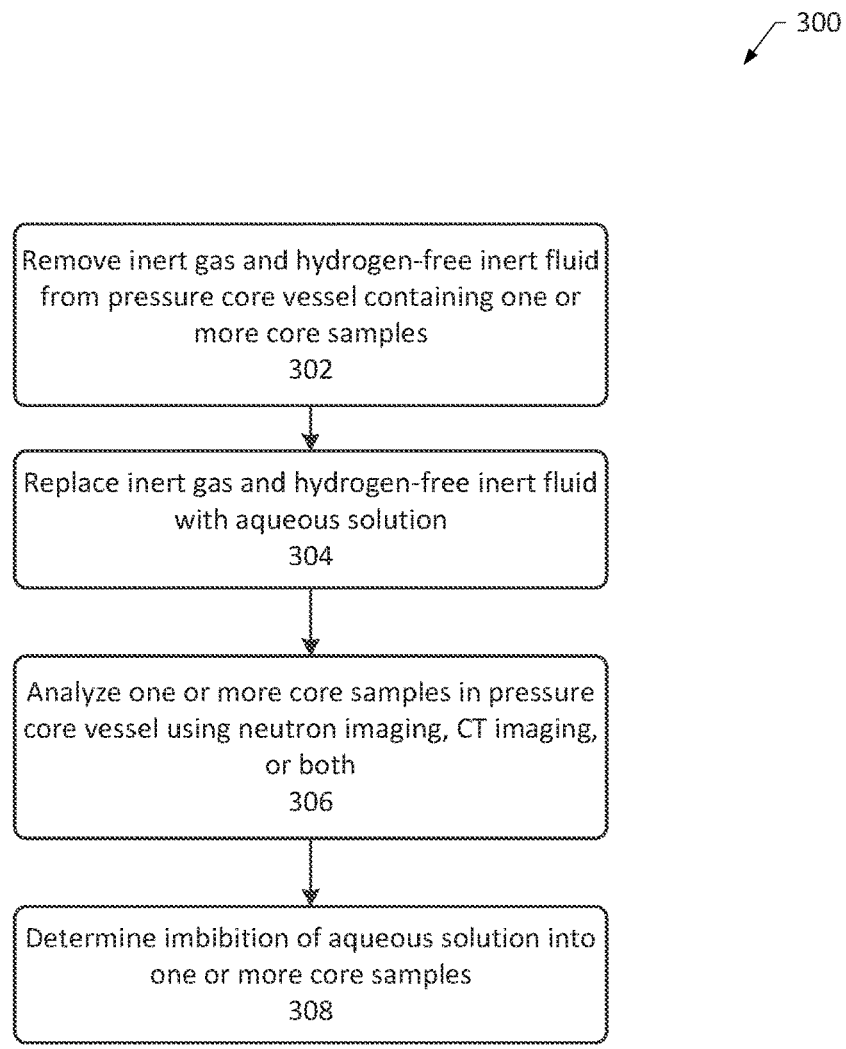
FIG. 3 is a block diagram of a process for determining imbibition of water by one or more core samples collected in accordance with an embodiment of the disclosure.
Figure 4:
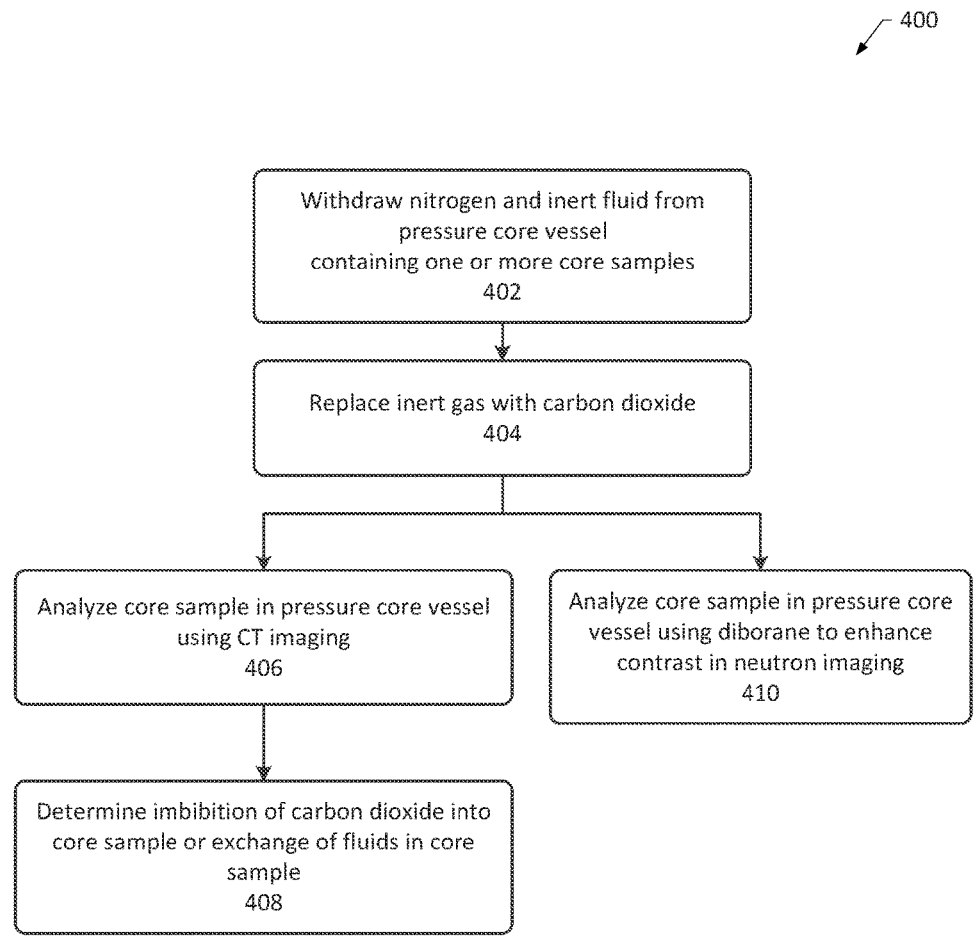
FIG. 4 is a block diagram of a process for determining imbibition of carbon dioxide by one or more core samples collected in accordance with an embodiment of the disclosure.

FIGS. 2-4 depict various processes for analyzing one or more core samples in a pressure core vessel (i.e., without opening the pressure core vessel and removing the one or more core samples) in accordance with embodiments of the disclosure. Accordingly, FIG. 2 depicts a process 200 for determining hydrocarbons-in-place from one or more core samples in a pressure core vessel collected and preserved in accordance with an embodiment of the disclosure. As explained below, pressure in the pressure core vessel may be reduced in steps until the pressure core vessel is depressurized to atmospheric pressure. At each reduction in pressure, the amount (e.g., volume) of fluid and gas released may be recorded and used in subsequent determinations.

As described above, a pressure core vessel containing one or more core samples immersed in a hydrogen-free fluid and containing a gas (e.g., an inert gas) may be obtained (202). If the pressure core vessel is not at the original reservoir pressure, the pressure core vessel having the one or more core samples may be pressurized to the original reservoir pressure (block 204). The pressure core vessel may be pressurized using a suitable pressurizing device or pressurized gas added to the pressure core vessel. Next, the pressure core vessel having the one or more core samples may be heated to the original reservoir temperature (block 206). For example, the pressure core sample may be heated using a suitable heating device.

Next, the pressure inside the pressurized pressure core vessel may be reduced by a pressure reduction value (block 208) by releasing and collecting gas, fluid, or both from the pressure core vessel. In some embodiments, the pressure reduction value may be based on the initial pressure inside the pressurized pressure core vessel, atmospheric pressure, a desired number of steps to depressurize the pressure core vessel to atmospheric pressure, or any combination thereof. The amount of gas and fluid released and collected during the pressure reduction may be recorded (block 210). After a pressure reduction, the pressure inside the pressure core vessel may be measured to determine if the pressure core vessel is at atmospheric pressure (decision block 212). If the pressure inside the pressure core vessel is not yet at atmospheric pressure (line 214), the pressure inside the pressurized pressure core vessel may be reduced by a pressure reduction value (block 208) and the amount of gas and fluid released and collected may be recorded (block 210) until the pressure inside the pressure core vessel is reduced to atmospheric pressure In some embodiments, each pressure reduction may reduce the pressure inside the pressure core vessel by the same pressure reduction value. In other embodiments, one or more pressure reduction steps may reduce the pressure inside the pressure core vessel by different pressure reduction values.

Once the pressure inside the pressure core vessel is determined to be at atmospheric pressure (line 216), the total amount (e.g., volume) of gas and fluids released may be calculated and used to determine the hydrocarbons-in-place of the reservoir (block 218). In some embodiments, after the determination of hydrocarbons-in-place described above the pressure core vessel may be opened and the one or more core samples may be transferred to another pressure vessel to monitor hydrocarbons released as a function of time.

In some embodiments, the one or more core samples in the pressure core vessel may be imaged during the depressurization to atmospheric pressure described above to determine the impact of depressurization on pressure sensitive petrophysical and mechanical rock properties. For example, in some embodiments, the one or more core samples may be imaged before, during, and after a pressure reduction by a pressure reduction value. In some embodiments, such pressure sensitive petrophysical and mechanical rock properties may include bulk modulus, shear modulus, Young's modulus, Poisson's ratio, shear velocity, compressional velocity, permeability, porosity, and clay swelling. In other embodiments, the impact of depressurization on other petrophysical and mechanical rock properties may be determined.

In some embodiments, images of pressurized one or more core samples in the pressure core vessel may be compared to images of depressurized one or more core samples in the pressure core vessel to quantify fracturing and damage introduced into the core samples during depressurization. For example, in such embodiments, images of the one or more core samples obtained before the first pressure reduction or after one or more pressure reductions may be compared to images of the one or more core samples obtained after depressurization to atmospheric pressure.

In some embodiments, imbibition of water into one or more core samples in the pressure core vessel may be determined. FIG. 3 depicts a process 300 for determining imbibition of water into one or more core samples in a pressure core vessel collected and preserved in accordance with an embodiment of the disclosure. After a pressure core vessel having one or more core samples is retrieved to the surface, the transferred gas and hydrogen-free fluid may be removed from the pressure core vessel (block 302) and replaced with an aqueous solution (block 304). The aqueous solution may include, for example, water or a water-based fluid.

Next, the one or more core samples in the pressure core vessel may be imaged using neutron imaging, computed tomography (CT) imaging, or a combination thereof (block 306). In some embodiments, the imaging of the one or more core samples may be performed before, during, and after imbibition of the aqueous solution. The imbibition of the aqueous solution into the core sample may be determined based on the resultant images (block 308). In some embodiments, the images of the one or more core samples before imbibition of the aqueous phase (and while the one or more core samples are immersed in the hydrogen-free fluid) may be compared to the images obtained during and after imbibition of the aqueous phase to identify water-wet pore space in the one or more core samples.

In some embodiments, imbibition of carbon dioxide ($CO_2$) into one or more core samples in the pressure core vessel may be determined. FIG. 4 depicts a process 400 for determining imbibition of carbon dioxide into one or more core samples in a pressure core vessel collected and preserved in accordance with an embodiment of the disclosure. After a pressure core vessel having one or more core samples is retrieved to the surface, the transferred gas and hydrogen-free fluid may be withdrawn from the pressure core vessel (block 402), and carbon dioxide may be added to the pressure core vessel (block 404). In such embodiments, pressure of the fluids in the pressure core vessel may be maintained during the addition of carbon dioxide.

Next, the core sample in the pressure core vessel may be analyzed using computed tomography (CT) imaging (block 406). For example, in some embodiments using CT imaging, the imbibition of carbon dioxide into the one or more core samples or exchange of fluids in the one or more core samples may be determined based on the imaging results (block 408). In other embodiments, other fluids may be used to enhance images of the one or more core samples generated by various imaging techniques. For example, in some embodiments, xenon may be used to enhance X-ray images (e.g., radiographic images and CT images). In another example, in some embodiments and as described above, the core sample in the pressure core vessel may be analyzed using diborane ($B_2H_6$) to enhance contrast in neutron imaging (block 410). In some embodiments, the images of the one or more core samples before imbibition or exchange of carbon dioxide or other gases may be compared to the images obtained during and after addition of the carbon dioxide or other gases to identify, for example, the imbibition of gases such as carbon dioxide into the one or more core samples or exchange of fluids in the one or more core samples.

Figure 5:
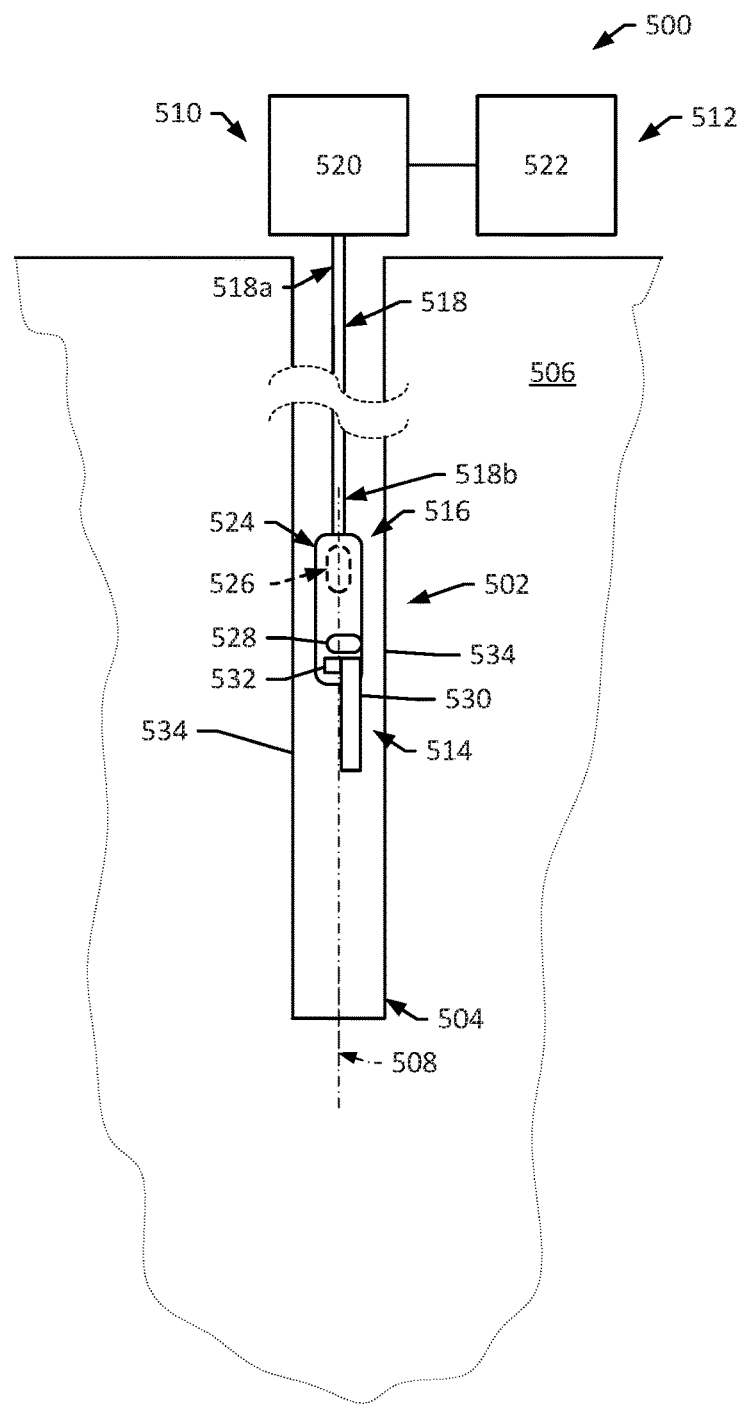
FIG. 5 is a block diagram of a rock and fluid sampling system employing a rock and fluid sampling tool in accordance with embodiments of the present disclosure.

FIG. 5 illustrates a rock and fluid sampling system 500 employing a rock and fluid sampling tool 502 in accordance with an embodiment of the disclosure. Embodiments of the disclosure may include, for example, the modification (e.g., retrofit) of existing commercial rock and fluid sampling systems to include the features and operations described herein. The borehole rock and fluid sampling system 500 includes rock and fluid sampling tool 502, a wellbore 504 (also referred to as the "borehole") formed in a reservoir 506 and having a longitudinal axis 508, a conveyance system 510, and a control system 512. As depicted in the illustrated embodiment, the fluid and sampling tool 502 may be disposed into the wellbore 504 with a lower end 514 entering the wellbore 504 first, followed by an upper end 516. Although FIG. 5 depicts the wellbore 504 and the rock and fluid sampling tool 502 in a generally vertical orientation, it should be appreciated that in other embodiments other orientations may be used.

The wellbore 504 may include any form of a hole formed in a geologic formation. In some embodiments, the wellbore 504 may include a wellbore created for the purpose of locating and extracting hydrocarbons or other resources from the reservoir 506. For example, the reservoir 506 may include an oil and gas reservoir, and the wellbore 504 may include a wellbore drilled into the reservoir 506 for the purpose of locating and extracting oil, gas and other hydrocarbons therefrom.

Although the illustrated portion of the wellbore 504 includes a substantially straight, vertical column, the wellbore 504 may take any variety of suitable shapes/directions. In some embodiments, the wellbore 504 may deviate from vertical along its length as a result lateral deviation of the drill bit during the drilling process (e.g., the drill bit inadvertently drifting—or sometimes being intentionally forced to drift—to left or right during the drilling process). As a further example, the wellbore 504 may include a directional borehole formed using directional drilling techniques. When inserted (e.g., lowered) into a borehole with varying direction, a tool may generally follow the direction of the borehole such that its axis remains substantially aligned with the axis of the boreholes.

The conveyance system 510 may provide for conveying (transporting) tools and equipment to and/or from a subsurface location. In some embodiments, the conveyance system 510 may be used to transport drilling bits, logging tools, perforating guns, fracturing fluids, and/or the like to and/or from a subsurface portion of the wellbore 504. For example, the conveyance system 510 may include devices for lowering the fluid and sampling tool 502 into the wellbore 504, and subsequently retrieving (raising) the fluid and sampling tool 502 therefrom. The type and configuration of the conveyance system 510 may vary based on the characteristics of the borehole and/or the tool or equipment being conveyed.

In some embodiments, the conveyance system 510 includes a conveying member 518 (e.g., a wireline) that facilitates transporting the fluid and sampling tool 502 and/or communication (e.g., electrical and data communications) between the fluid and sampling tool 502 and surface systems. The conveying member 518 may include a first (upper) end 518a coupled to a surface conveyance unit 520 and a second (lower) end 518b coupled to the fluid and sampling tool 502. The type of the conveying member 510 and/or the surface conveyance unit 520 may vary based on the conveyance technique being employed. For example, if the conveyance system 510 is a wireline system, the conveying member 518 may include a wireline cable and the surface conveyance unit 520 may include a wireline spool. In another example, if the conveyance system 510 is a drill pipe system, the conveying member 518 may include drill pipe and surface conveyance unit 520 may include a drilling rig. As yet another example, if the conveyance system 510 is a coiled tubing (CT) system, the conveying member 518 may include coiled tubing (CT) (e.g., including a wireline disposed therein) and the surface conveyance unit 520 may include a CT spool. In some embodiments, the conveyance system 510 may include a tractor conveyance device. A tractor may be used in place of or in combination with one of the above described conveyance techniques. For example, the conveyance system 510 may include both a wireline type conveying member 518 and a down-hole tractor that is disposed above or below the fluid and sampling tool 502 to provide physical force to assist in pushing and/or pulling the fluid and sampling tool 502 up and/or down through the wellbore 504.

The control system 512 may control various operational aspects of the rock and fluid system 200. For example, the control system 512 may include control circuitry and processing systems to provide monitoring and/or control of well drilling, completion and production operations. In some embodiments, the control system 512 includes a rock and fluid sampling control system 522 that provides for monitoring and/or controlling sampling operations using the fluid and sampling tool 502. For example, the rock and fluid sampling control system 522 may control the conveyance system 510 based on feedback provided by the conveyance system 510 and/or the fluid and sampling tool 502. The feedback may include, for example, depth measurements returned from conveyance system 510, data received from the fluid and sampling tool 502, or both.

The rock and fluid sampling tool 502 may include various components to enable collection and preservation of core samples in accordance with the techniques described herein. As shown in FIG. 5, in some embodiments the rock and fluid sampling tool 502 may include a tool body 524, tool electronics 526, a rotary sidewall coring device 528, a pressure core vessel 530, and a gas storage and valving system 532.

The tool body 524 may house various components of the fluid and sampling tool 524. In some embodiments, the tool body 524 may include a rigid structure, such as a metal cylinder. Such a rigid structure may enable components to be permanently or removably affixed thereto. In such embodiments, the tool body 524 may protect the tool electronics 526, a rotary sidewall coring device 528, and other components from damage during use (e.g., when fluid and sampling tool 502 is lowered into the wellbore 504 during a sampling operation).

The tool electronics 526 may include circuitry (e.g., implemented in processing devices) that facilitate control of various operational aspects of the fluid and sampling tool 502. For example, the tool electronics 526 may control the rotary sidewall coring device 528 and obtaining of samples from the wellbore 504. In some embodiments, the tool electronics 526 may facilitate communication with other devices of the fluid and sampling system 500. For example, during a sampling operation the tool electronics 526 may receive a command (e.g., a command from a control system) to initiate the collection of a core sample. In response to the command, the tool electronics 526 may send the appropriate commands to the rotary sidewall coring device 528. In another example, the tool electronics 526 may receive a command to complete collection of core samples and may initiate sealing of the pressure core vessel 530 and injection with a gas via the gas storage and valving system 532.

As noted above, the rotary sidewall coring device 528 may enable the collection of core samples from a sidewall 534 of the wellbore 504. In some embodiments, the rotary sidewall coring device 528 may extend from the tool body 524 and engage the sidewall 534. After collection of a core sample from the sidewall 534 of the wellbore 504, the rotary sidewall coring device 528 may place the collected core sample in the pressure core vessel 530. As describe above, the pressure core vessel 530 may be filled with a hydrogen-free fluid such that placing the core sample in the pressure vessel 530 immerses the core sample in the hydrogen-free fluid (and displaces a corresponding amount of hydrogen-free fluid).

The pressure core vessel 530 may be fully enclosed by the tool body 524 or, in some embodiments, may partially protrude from the tool body 524. The pressure core vessel 530 may be formed from metal and, in the embodiments described herein, may be include a eutectic metal component. In some embodiments, the eutectic metal may be selected based on melting temperature, melting/solidification rate, composition (e.g., interference with imaging techniques such as NMR imaging), or any combination thereof. In some embodiments, the pressure core vessel 530 may include a cap that seals the pressure vessel 530 after collection of core samples from the wellbore 504.

The gas storage and valving system 532 may include suitable components for storing a gas and inserting the gas into the pressure core vessel 532. For example, in some embodiments the gas storage and valving system 532 may include a pressurized container (e.g., gas cylinder) storing a pressurized gas (e.g., nitrogen). Additionally, in some embodiments the gas storage and valving system 532 may include one or more lines and one or more valves coupling the pressurized container to the pressure core vessel 530 to enable insertion of the gas into the pressure core vessel 530. For example, upon the completion of the collection of core samples from the wellbore 504, the gas may be added to the pressure core vessel 530 by opening the appropriate valve or valves until a desired pressure or volume of gas has been added to the pressure core vessel 530. In some embodiments, various sensors (e.g., pressure sensors) may be included in the gas storage and valving system 532, the pressure core vessel 530, or both to enable monitoring of the gas.

Figure 6:
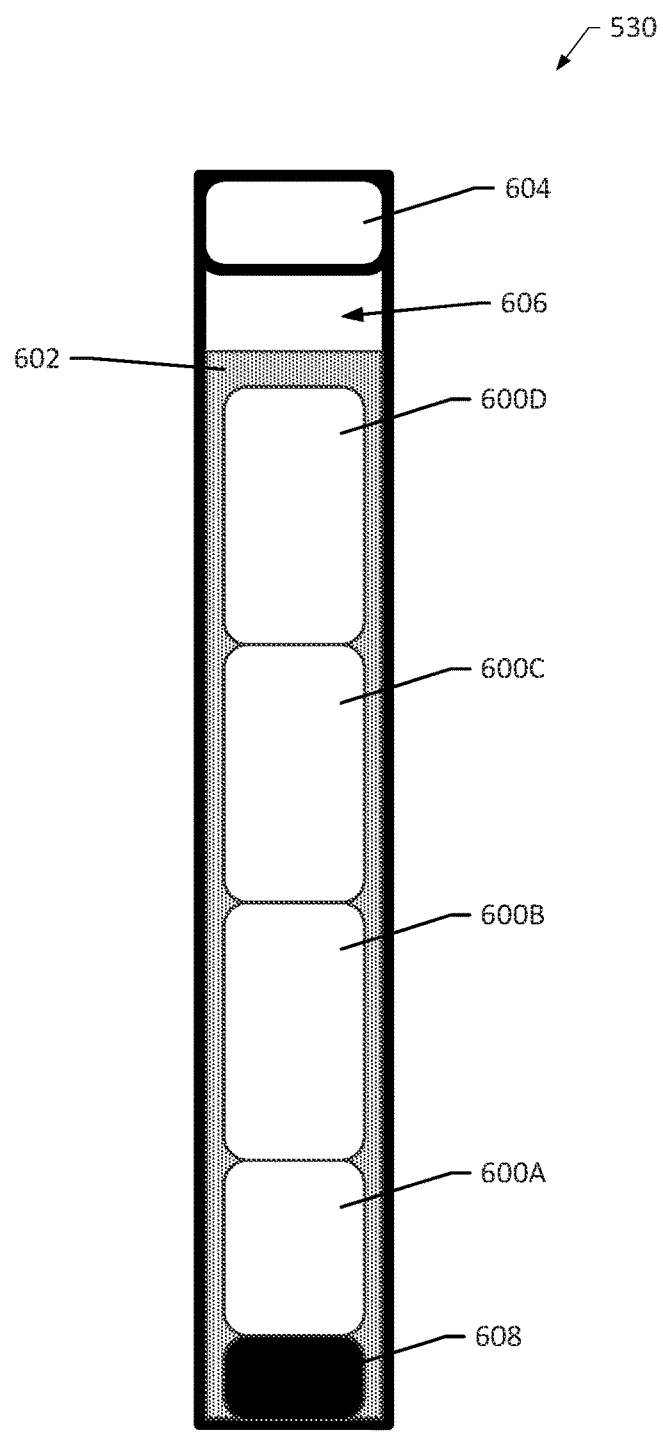
FIG. 6 is a block diagram of a pressure core vessel of a rock and fluid sampling tool in accordance with embodiments of the present disclosure.

FIG. 6 depicts a schematic view of the pressure core vessel 530 showing core samples 600 collected and preserved in accordance with an embodiment of the disclosure. As shown in FIG. 5, the pressure core vessel 530 may contain a first core sample 600A, a second core sample 600B, a third core sample 600C, and a fourth core sample 600D. It should be appreciated that, in other embodiments, a pressure core vessel may store any suitable number of core samples, such as one or more core samples, two or more core samples, three or more core samples, four or more core samples, five or more core samples, six or more core samples, seven or more core samples, eight or more core samples, nine or more core samples or ten or more core samples.

In some embodiments, the pressure core vessel 530 may be generally cylindrical-shaped. In other embodiments, the pressure core vessel 530 may be other shapes. The pressure core vessel 530 may be formed from metal. In some embodiments, as discussed above, the pressure core vessel 530 may include a eutectic metal insert 608. In some embodiments, some portions of the pressure core vessel 530 may be formed from a metal and other portions may be formed from other materials.

In some embodiments, for example, the each of the core samples 600 may be collected at different depths in the borehole. For Example, the first core sample 600A may be collected at a first depth, the second core sample 600B may be collected at a second depth (e.g., a second depth greater than the first depth), and so on. As shown in FIG. 6 and as mentioned above, the pressure core vessel 530 may be filled with a hydrogen-free fluid 602. As each core sample is added to the pressure core vessel 530, the hydrogen-free fluid 602 is displaced in the pressure core vessel 530 and covers the core sample. Thus, as shown in FIG. 6, the level of hydrogen-free fluid 602 is above the fourth core sample 600D such that all core samples 600A, 600B, 600C, and 600D are immersed in the hydrogen-free fluid 602.

In some embodiments, the pressure core vessel 530 may be sealed via a sealing cap 604. In some embodiments, for example, the sealing cap 604 may include one or more sealing components (e.g., O-rings) that engage the walls of the pressure core vessel 530 and seal the pressure core vessel 530. In some embodiments, the sealing cap 604 may include a component for connection to the gas storage and valving system 532 to enable the addition of a gas to the pressure core vessel 530. As discussed above, a gas may be added to the pressure core vessel 530 to fill the space 606 unoccupied by the hydrogen-free fluid 602 and the core samples 600. Thus, some space 606 of the pressure core vessel 530 shown in FIG. 6 may be filled with a gas to mitigate or prevent pressure loss and maintain the original pressure of the core samples 600 as the pressure core vessel 530 is retrieved to the surface.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described herein. It is to be understood that the forms shown and described herein are to be taken as examples of embodiments. Elements and materials may be substituted for those illustrated and described herein, parts and processes may be reversed or omitted, and certain features may be utilized independently, all as would be apparent to one skilled in the art after having the benefit of this description. Changes may be made in the elements described herein without departing from the spirit and scope of the disclosure as described in the following claims. Headings used herein are for organizational purposes only and are not meant to be used to limit the scope of the description.

What is claimed is:

1. A rock and fluid sampling tool, comprising:
a rotary sidewall coring device;
a vessel comprising a eutectic metal component, the vessel configured to contain one or more core samples of a reservoir, the one or more core samples obtained by the rotary sidewall coring device from a sidewall of a wellbore extending from a surface into a reservoir,
a container configured to store a gas; and
one or more valves connecting the container to the vessel.

2. The system of claim 1, wherein the rock and fluid sampling tool comprises a wireline rock and fluid sampling tool.

3. The system of claim 1, wherein the gas is nitrogen.

4. The system of claim 1, wherein the vessel contains a hydrogen-free fluid.

5. The system of claim 1, wherein the hydrogen-free fluid comprises a fluorocarbon-based fluid.

6. A method of collecting one or more core samples from a wellbore, comprising:
inserting a rock and fluid sampling tool in a wellbore extending from a surface into a reservoir;
extracting a core sample from a sidewall of the wellbore;
placing the core sample in a vessel, the vessel containing a hydrogen-free fluid;
sealing the vessel;
transferring a gas into the vessel; and
retrieving the vessel to the surface.

7. The method of claim 6, wherein inserting a rock and fluid sampling tool in a wellbore comprises inserting the rock and fluid sampling tool on a wireline inserted in the wellbore.

8. The method of claim 6, wherein the hydrogen-free fluid comprises a fluorocarbon-based fluid.

9. The method of claim 6, wherein the gas comprises nitrogen.

10. The method of claim 6, wherein the vessel comprises a eutectic metal component.

* * * * *